United States Patent [19]

Salo et al.

[11] Patent Number: 4,686,987
[45] Date of Patent: Aug. 18, 1987

[54] BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND

[75] Inventors: Rodney W. Salo, Columbia Heights; Brian D. Pederson, St. Paul, both of Minn.

[73] Assignee: Cardiac Pacemakers, Inc., St. Paul, Minn.

[21] Appl. No.: 362,903

[22] Filed: Mar. 29, 1982

Related U.S. Application Data

[63] Continuation-in-part of Ser. No. 274,875, Jun. 18, 1981, abandoned.

[51] Int. Cl.$^4$ .............................................. A61N 1/36
[52] U.S. Cl. .............................................. 128/419 PG
[58] Field of Search ................ 128/419 PG, 693, 694, 128/713, 723, 734, 782

[56] References Cited

U.S. PATENT DOCUMENTS

| | | | |
|---|---|---|---|
| 3,316,896 | 5/1967 | Thomasset | 128/734 |
| 3,587,562 | 6/1971 | Williams | 128/723 |
| 3,742,936 | 7/1973 | Blanie et al. | 128/693 |
| 4,137,910 | 2/1979 | Murphy | 128/713 |
| 4,303,075 | 12/1981 | Heilman et al. | 128/419 PG |
| 4,313,442 | 2/1982 | Knudson et al. | 128/419 PG |

Primary Examiner—William E. Kamm
Attorney, Agent, or Firm—Orrin M. Haugen; Thomas J. Nikolai

[57] ABSTRACT

A biomedical apparatus capable of sensing changes in the heart's ventricular volume or stroke volume and then changing the operating performance of the device in a fashion as a function of stroke volume. A relatively low frequency signal (under 5 KHz) is applied between spaced electrodes disposed in the heart and the beating action of the heart serves to modulate this signal due to changes in impedance being sensed between these or other electrodes within the heart. The modulated carrier signal is then processed to remove R-wave and other electrical artifacts and then demodulated to remove the carrier frequency component leaving the envelope which is proportional to instantaneous ventricular volume. This envelope signal then contains stroke volume and ventricular volume information which can be used by the biomedical apparatus to vary its operating parameters. For example, a current proportional to changes in stroke volume may be injected into the timing circuit of a demand-type cardiac pacer pulse generator whereby the interpulse interval of the pulse generator is varied as a function of stroke volume.

14 Claims, 8 Drawing Figures

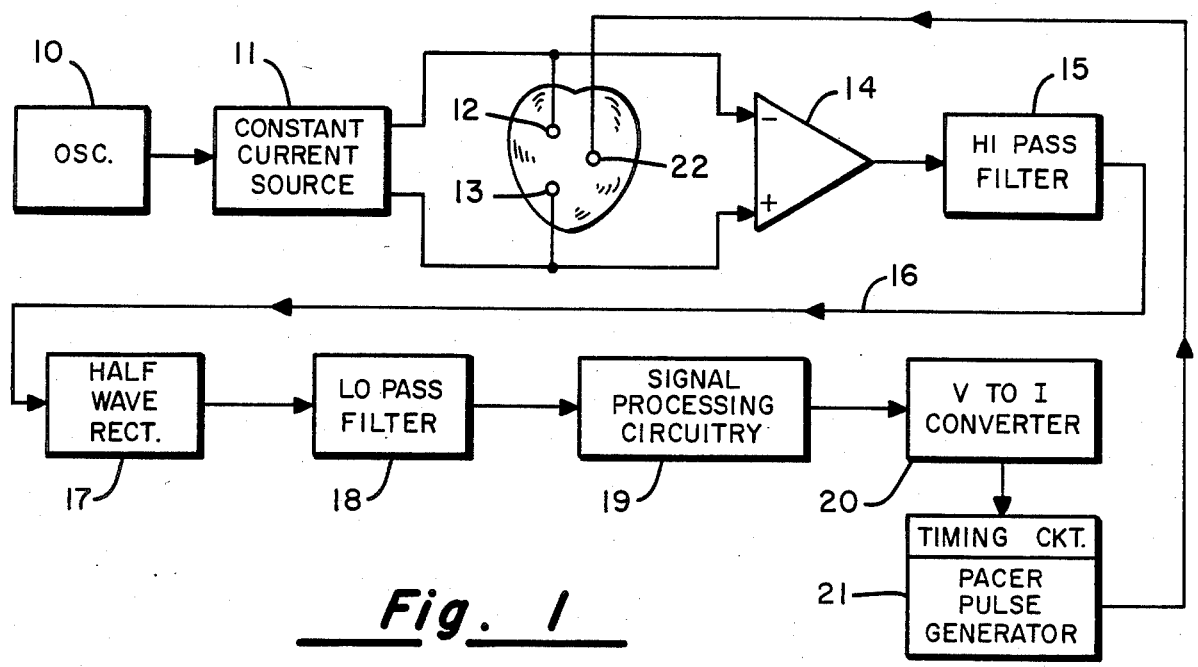
_Fig. 1_
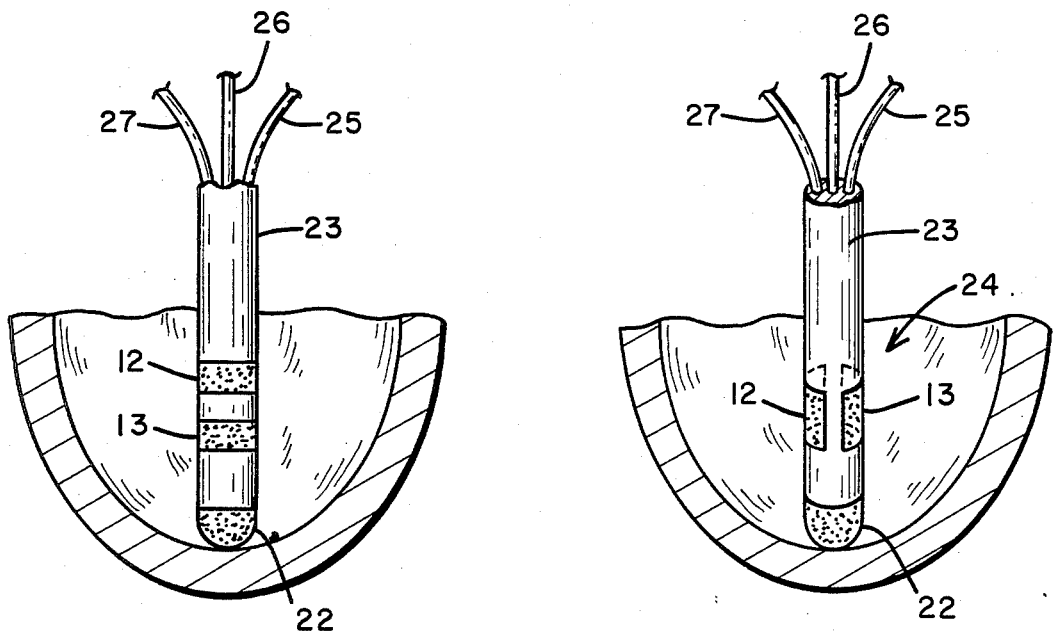
_Fig. 2_     _Fig. 3_

4,686,987

BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND

CROSS-REFERENCE TO RELATED APPLICATION

This is a continuation-in-part application of now abandoned application Ser. No. 274,875, filed June 18, 1981 and entitled VARIABLE RATE PACER RESPONSIVE TO CHANGES IN STROKE VOLUME.

BACKGROUND OF THE INVENTION

The stroke volume of the heart is defined as the volume of blood expelled by a ventricle in a single beat. It is equal to the difference between end diastolic volume and end systolic volume. The importance of stroke volume in determining the state of the heart is evident in that the cardiac output, i.e., the total volume of blood pumped by a ventricle during a period of time, is equal to the product of the heart rate and the stroke volume. The stroke volume may be increased either by decreasing the end systolic volume, implying increased myocardial shortening. or by increasing end diastolic volume. Increases in ventricular distention result in greatly increased wall tension to develope the same intraventricular pressure during ejection.

In normal human subjects with healthy hearts, the stroke volume of the heart remains relatively constant over a wide range of exertion, from minimal activity to high physical exertion. The increases in cardiac output under stress are due primarily to increased heart rate, at least up to a point. Also, in normal human subjects, increases in stroke volume are reported only under maximal exercise conditions as the heart rate tends to level off. In contrast, with patients suffering from third degree heart block where a fixed rate cardiac pacer is determining the heart rate, increased cardiac output during exertion is due principally to increased stroke volume. However, stroke volume cannot increase by more than a factor of 2 to 2½ which limits the exercise capabilities of these patients.

Because stroke volume, in individuals with a fixed heart rate due to heart block, is a useful indicator of cardiovascular load, and since studies indicate a constancy of stroke volume under sub-maximal exercise, it would be advantageous to have a cardiac pacer having a variable rate and a means for varying that rate as a function of stroke volume. In such an arrangement, during exercise, the pulse generator would be designed to sense the increase in stroke volume due to changes in physiologic demand and would function to increase the pulse rate so as to bring the stroke volume parameter back to its original value.

In a paper entitled "Continuous Measurement of Ventricular Stroke Volume by Electrical Impedance" published in the *Cardiovascular Research Center Bulletin*, Volume 4, No. 4, April–June 1966, Pages 118 through 131, L. A. Geddes and his associates at the Baylor University College of Medicine in Houston, Texas reported on an approach for measuring stroke volume by sensing changes in impedance between two spaced electrodes disposed within the ventricular cavity. It was theorized that the blood in the ventricle constitutes an electrical conductor of irregular and changing shape such that spaced electrodes placed in the ventricle could be used to sense instantaneous impedance variations observed between the electrodes as the blood fills and leaves the ventricle.

In the Knudson et al application Ser. No. 170,947, filed July 21, 1980, now U.S. Pat. No. 4,313,442 there is described a cardiac pacer whose rate of generation of pacer pulses is controllable as a function of changes in the detected P-wave rate. In that arrangement, a lead having a stimulating electrode at its distal tip is positioned so that the electrode abuts the apex of the ventricle. That lead has further sensing electrodes disposed a predetermined distance proximally of the tip of the stimulating electrode so as to be located near the upper right wall of the atrium. The atrial (P-wave) activity picked up by the sensing electrodes is processed in suitable circuitry and used to vary the interpulse interval of a demand-type cardiac pacer. In that the P-wave activity is indicative of physiologic demand, the variable rate pacer of the aforesaid Knudson et al patent permitted the stimulating rate to be altered as a function of body needs.

When the present invention is used in conjunction with a cardiac pacer having a variable rate capability, P-wave activity is no longer an indicator of physiologic demand, but instead, changes in stroke volume are detected and a signal is developed which is proportional to those changes. By applying that signal as a control signal to the timing circuit of a demand-type cardiac pacer, the pacer pulse generator will output stimulating pulses in accordance with the physiologic demand indicated by stroke volume changes. The method and apparatus of the present invention as applied to a cardiac pacer involves varying the ventricular pacing rate in such a fashion as to minimize changes in stroke volume. Thus, during exercise, the sensing circuitry to be described senses changes in ventricular volume or stroke volume and then alters the operating parameters of the utilization device. For example, in a cardiac pacer application, increases in stroke volume may be sensed and the resulting control signal may be used to increase the pulse rate so as to bring the stroke volume back to its original value. This may be done either with respect to an absolute reference stroke volume or, as in the system of the aforereferenced Knudson patent, by sensing only changes in stroke volume and altering the rate to minimize the changes.

SUMMARY OF THE INVENTION

In carrying out the instant invention, a lead arrangement having a stimulating tip adapted to abut the apex of the right ventricle has further sensing electrodes in the form of either axially spaced apart rings or rings which are split so as to form two radially spaced arcuate segments which are disposed proximally of the tip by a distance which locates those sensing electrodes or segments solely within the ventricle. A relatively low frequency, low amplitude, alternating current signal, typically in the range between 0.5 and 5 KHz and between 1.0 and 10 microamperes (RMS) is applied across the spaced electrodes and it is found that the beating action of the heart and the accompanying changes in blood volume within the monitored ventricle results in a modulation of the AC signal, the modulating envelope being proportional to stroke volume. The modulated carrier wave is then filtered, demodulated, and signal processed to produce a current signal which is proportional to the stroke volume of the heart. This current may be injected into the timing circuit of a cardiac pacer whereby the escape interval of the pacer is controlled as a function of changes in stroke volume. Alternatively, the demodulated waveform or the current signal proportional to changes in stroke volume may be used in other biomedical electronic apparatus such as a drug dispensing pump, surgical monitoring equipment, a cardiac output computer, an arrithymia monitor, etc.

DESCRIPTION OF THE DRAWINGS

FIG. 1 represents by means of a block diagram a system incorporating the present invention;

FIG. 2 illustrates one form of lead arrangement useful in practicing the invention;

FIG. 3 illustrates an alternative lead construction which may be used in practicing the invention;

DESCRIPTION OF THE PREFERRED EMBODIMENT

Figures 4, 4A:
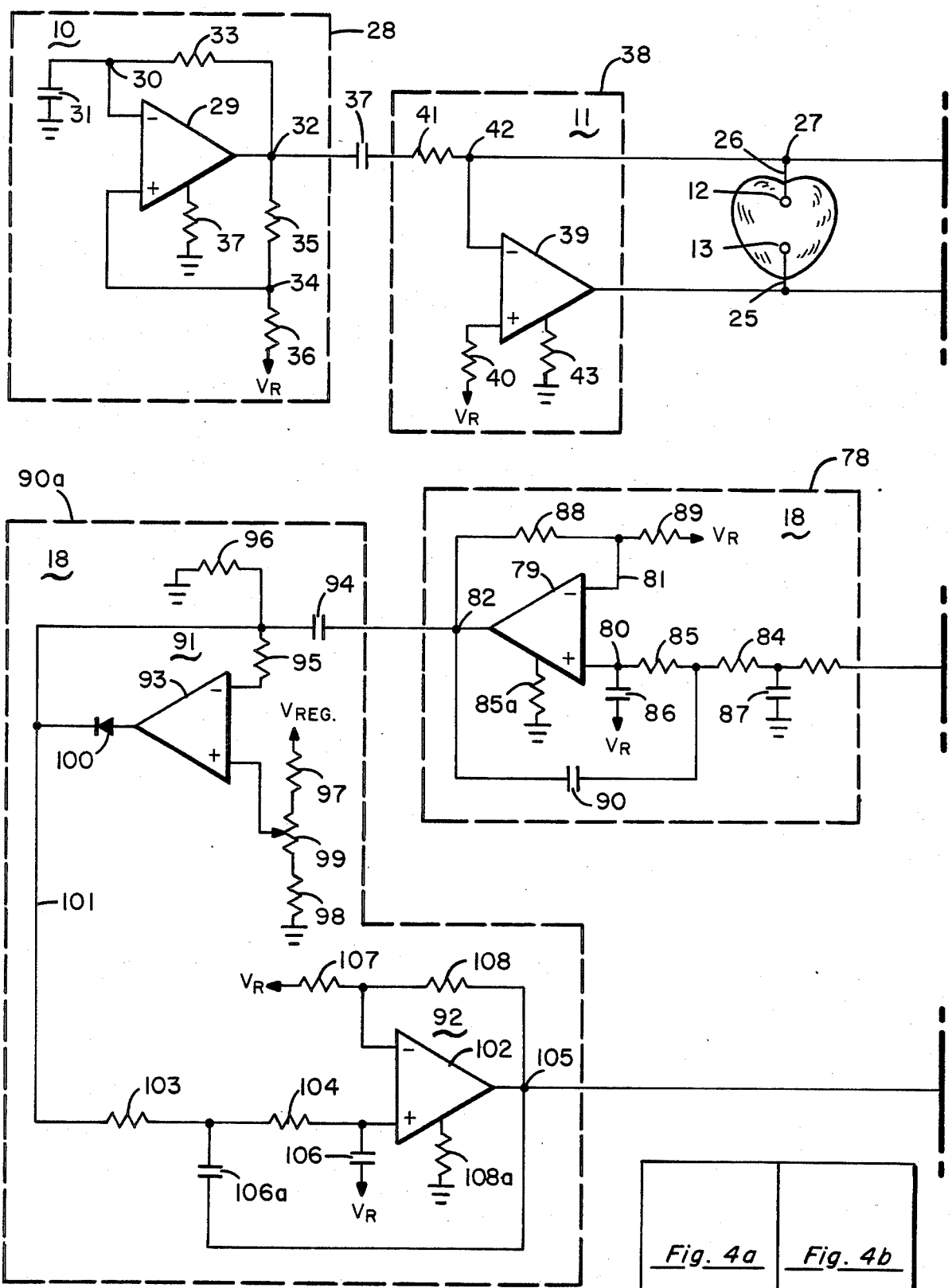
FIG. 4 is an electrical schematic diagram of a circuit for producing a control signal proportional to changes in the stroke volume of a mammalian heart from an absolute reference.
Figure 4B:
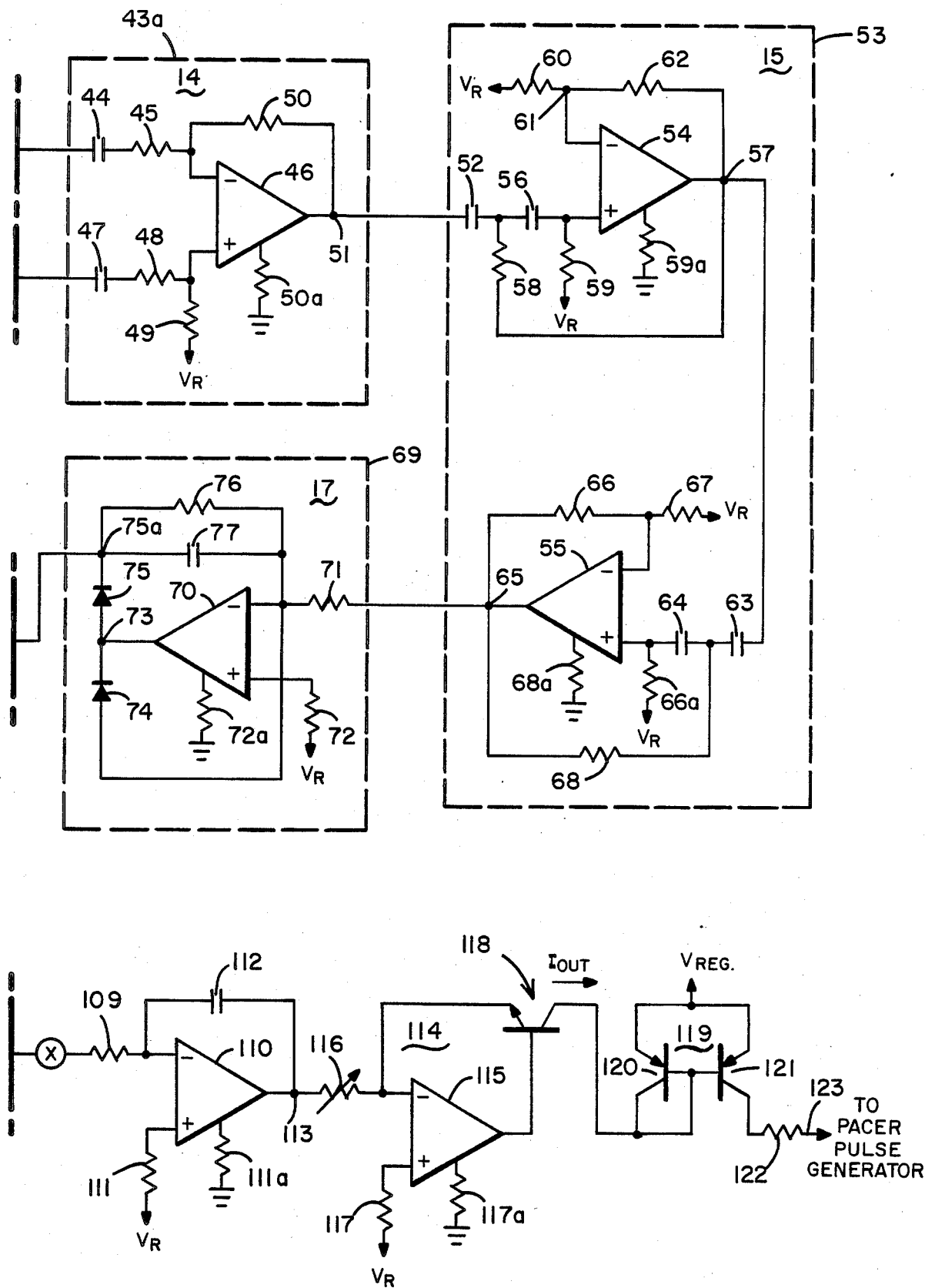

Referring first to FIG. 1, there is shown an oscillator circuit 10 whose output is coupled through a constant current source 11 to first and second spaced apart electrodes 12 and 13 that are located in the ventricle of the heart, and disposed upon a lead which connects to the output of the constant current source 11. The oscillator is arranged to produce pulses at a frequency which is quite high compared to the heart rate, typically in the range of from 500 to 1000 Hz. A differential amplifier 14 has its inverting input coupled via a conductor in the lead to the electrode 12 and its non-inverting input is coupled by a separate conductor also contained within the lead to the electrode 13. The output from the differential amplifier 14, which is in the form of a modulated carrier wave, is applied to a high pass filter circuit 15 and from there, the output is fed over a conductor 16 to a half-wave rectifier network 17. The half-wave rectifier provides its output to a low pass filter 18 which removes the carrier signal and from there, the envelope signal is applied through further signal processing circuitry 19 to a voltage-to-current converter circuit 20. When the stroke volume sensing circuitry heretofore described is to be used to control the pacing rate of a cardiac pacer, the output from the circuit 20 may be coupled to the timing circuit portion of an implantable pulse generator 21 whose output is coupled through a further conductor in the lead to a stimulating electrode 22 disposed in or on the heart. The signal from the V-to-I converter 20 applied to the pulse generator's timing circuit may be proportional either to absolute stroke volume or to change in stroke volume, depending upon the manner in which the output signal from the low pass filter stage is processed.

Before going into a detailed explanation of an implementation of a circuit conforming to the block diagram of FIG. 1, it may be helpful to consider the design of the lead structures which may be used in combination with the preferred embodiment for effecting rate change as a function of the stroke volume parameter of the patient's heart. In this regard, FIG. 2 illustrates one form of lead and electrode structure which may be used. In this figure there is shown an endocardial lead 23 having a tip electrode 22 arranged to be disposed in the apex of the right ventricle and spaced proximally of this tip electrode along the axis of the lead 23 are the conductive ring electrodes 12 and 13 used for sensing variations in impedance existing between them. It has been found that during systole, as the cross-sectional area of the heart decreases, a corresponding increase is noted in the impedance existing between the sensing electrodes 12 and 13.

In FIG. 3 there is shown an alternative lead configuration wherein a single ring element identified generally by numeral 24 is slit along a diameter so as to yield two generally cylindrical surfaces spaced apart from one another radially, rather than axially, in forming the electrode members 12 and 13.

In the embodiments of both FIGS. 2 and 3, the lead comprises an insulating sheath 23 surrounding three conductors 25, 26 and 27 which respectively couple the sensing electrodes 12 and 13 and the stimulating tip electrode 22 to the implanted pulse generator. The electrodes 12 and 13 are disposed on the outer surface of the insulative sheath 23 where they are exposed to body fluids when implanted.

With the two ring electrode configuration of FIG. 2 the system may be modeled by a volume conductor of fixed length (the distance between the rings 12 and 13) and variable cross-sectional area. With this electrode configuration, the cross-section is perpendicular to the longitudinal axis of the right ventricle in which the lead is adapted to be inserted. From the well-known formula for computing electrical resistance $R = P(l/A)$, it is apparent that a decrease in cross-sectional area (A) which takes place during systole will result in a corresponding increase in the resistance measured between the two spaced electrodes. Likewise the increase in cross-sectional area as blood fills the ventricles during diastole results in a decrease in the resistance measured between the two spaced electrodes.

In the split-ring electrode configuration illustrated in FIG. 3, there is the advantage of increased sensitivity in that both longitudinal and radial motion of the ventricular wall results in larger measured impedance changes. A further advantage of the electrode configuration of FIG. 3 is that it exhibits improved pacer spike rejection due to the symmetric positioning of the rings with respect to the tip electrode 22. Offsetting these distinct advantages is the fact that the impedance measurement obtained by the split-ring sensing electrode arrangement is dependent somewhat on lead orientation. It can be shown that the change in impedance measurable using the split-ring electrodes decreases as a cosine function of the angle between the maximum width dimension of the right ventricle and a line extending perpendicular to the axial gap between the split-ring segments 12 and 13.

FIG. 4 illustrates a schematic electrical diagram of a circuit arrangement implementing the system represented diagrammatically in FIG. 1. In this schematic, the oscillator 10 comprises an astable multivibrator and is shown as being enclosed by the broken line box 28. It includes an operational amplifier 29 whose inverting input terminal 30 is coupled through a capacitor 31 to a point of reference potential, such as ground, and whose output terminal 32 is coupled through a feedback resistor 33 to the operational amplifier's inverting input terminal 30. The non-inverting input of that amplier is, in turn, coupled to a junction point 34 between series connected resistors 35 and 36, the remaining terminal of the resistor 35 being coupled to the output terminal 32 of the operational amplifier and the remaining terminal of the resistor 36 being coupled to a point of reference potential $V_R$. A resistor 37 is coupled between the bias supply terminal of the operational amplifier 29 and ground.

The output from the square wave oscillator 10 is capacitively coupled by a capacitor 37 to the constant current source 11 which is illustrated as being enclosed by the broken line box 38. The constant current source 11 includes an operational amplifier 39 whose non-inverting input is coupled through a resistor 40 to the source of reference potential, $V_R$, and a resistor 41 joins the coupling capacitor 37 to a junction point 42 which is tied directly to the inverting input of the operational amplifer 39. A bias resistor 43 is connected in a conventional fashion to the operational amplifier 39 and to a point of fixed reference potential (ground).

The output from the constant current source 11 is coupled by one of the conductors 25 in the lead 23 to a sensing electrode 13. The remaining electrode 12 is coupled through a conductor 26 in the lead 23 to a terminal 27 which is tied directly to the aforementioned terminal 42 of the constant current operational amplifier stage 39. As the heart in which the lead 23 is implanted beats, changes in the volume of blood present in the right ventricle changes and these changes are reflected as a modulation of the output signal from the oscillator 10. The high frequency signals from the oscillator may be considered as a carrier wave and the wave is amplitude modulated by the impedance changes detected by the sensing leads and electrodes. The carrier may typically have a frequency of 1000 Hz, but limitation to this frequency is not intended. It is found that a carrier having a frequency of about 1000 Hz and an amplitude in the 1- to 10-microampere range does not produce unwanted tissue stimulation. As such, the likelihood of inducing cardiac arrythmias (tachycardia) is minimized.

The modulated carrier signal is fed to a differential amplifer stage 14 (shown enclosed by broken line box 43a) which provides a predetermined gain to the detected waveform. Specifically, the signal picked up on electrode 12 is fed through a coupling capacitor 44 and a resistor 45 to the inverting input of an operational amplifier 46. In a like fashion, the signal developed on the electrode 13 is coupled through a coupling capacitor 47 and a resistor 48 to the non-inverting input of the operational amplifier 46. The non-inverting input is also coupled through a resistor 49 to the source of reference potential $V_R$. A feedback resistor 50 joins the output terminal 51 of the differential amplifier stage 14 back to the inverting input terminal of the operational amplifier 46.

The amplified modulated carrier signal from the differential amplifier 46 is coupled to an active high pass filter stage 15. The high pass filter stage is shown as being enclosed by the broken line box 53. It includes a first operational amplifier 54 and a second operational amplifier 55. Capacitor 52 applies the signal from the differential amplifier 46, via a further capacitor 56, to the non-inverting input of the operational amplifier 54. The output terminal 57 of the operational amplifier 54 has a resistor 58 joining it to the junction point between the capacitors 52 and 56. A bias resistor 59 is connected at one terminal directly to the non-inverting input of the amplifier stage 54 and at its other terminal to the source $V_R$. A further resistor 60 is connected between the same source $V_R$ and the inverting input terminal 61 of the operational amplifier 54. A feedback resistor 62 joins the output terminal 57 of that amplifier to the inverting input. That output is capacitively coupled via condensers 63 and 64 to the non-inverting input of the operational amplifier 55. Its output terminal 65 is coupled via series connected resistors 66 and 67 to the reference source $V_R$ and via resistor 68 to the junction point between the series connected capacitors 63 and 64. The inverting input of the second stage of the high pass filter network connects to the common terminal between the series connected resistors 66 and 67.

The high pass filter stage 15 is a four-pole device which is effective to pass the modulated carrier signal. However, the common-mode rejection afforded by the differential amplifier stage 14 and the high pass filter stage 15 cooperate to significantly suppress ECG artifacts such as R-waves or pacer spikes which may be picked up by the sensing electrodes. Furthermore, the high pass filter serves to remove all other artifacts, excepting the carrier signal which carries the impedance information in the form of low frequency amplitude modulation thereof.

Shown enclosed by the broken line box 69 is a half-wave rectifier circuit 17. It comprises an operational amplifier stage 70 having its inverting input coupled through a resistor 71 to the output junction 65 of the high pass filter stage 15. The non-inverting input of the amplifier 70 is coupled through a resistor 72 to the reference source $V_R$. A first diode has its cathode connected to the output terminal 73 of the operational amplifier 70 and its anode terminal connected to the inverting input of that amplifier. A series circuit including a further diode 75 and a parallel combination of a resistor 76 and a capacitor 77 is coupled between that same output terminal 73 and the inverting input of the operational amplifier 70. With the diodes 74 and 75 poled as shown, only positive excursions of the modulated carrier are reproduced at the output terminal 75a.

Following rectification, the resulting signal is applied to a three-pole low pass filter circuit 18 which is shown in FIG. 4 as being enclosed by the broken line box 78. This low pass filter includes an operational amplifier 79 having a non-inverting input terminal 80, an inverting input terminal 81 and an output terminal 82. The output terminal 75a of the half-wave rectifier is coupled through a series string of resistors 83, 84 and 85 to the non-inverting input terminal 80. A capacitor 86 couples that same input terminal to a source of reference potential $V_R$. A further capacitor 87 is coupled between ground and the junction point between the series connected resistors 83 and 84. A feedback resistor 88 joins the output terminal 82 of the operational amplifier 79 back to its inverting input terminal 81. This same inverting input terminal 81 is coupled through a resistor 89 to the voltage source $V_R$. A feedback capacitor 90 connects between the output terminal 82 of the operational amplifier 79 and the junction formed between the series connected resistors 84 and 85.

The component values of the low pass filter circuit are chosen such that it exhibits an upper cut-off frequency of about 5 Hz. As such, the low pass filter stage 18 is effective to strip away the carrier signal, leaving only the envelope waveform. This envelope waveform is found to bear a close resemblance to the published stroke volume waveforms reported by Geddes et al, supra.

The demodulated envelope signal is applied through additional signal processing stages shown enclosed by broken line box 90a so that it may ultimately be used to perform a controlling function on a utilization device, such as to modify the timing circuit of a cardiac pacer pulse generator in a fashion to vary the rate at which stimulating pulses are generated as a function of measured stroke volume. This further signal processing circuitry includes a DC restorer network indicated generally by numeral 91 and a further low pass filter stage indicated generally by numeral 92. The DC restorer includes an operational amplifier 93 whose inverting input is coupled through a capacitor 94 and a resistor 95 to the output from the low pass filter 18.

The resistor 95 comprises a portion of a voltage divider which also includes a resistor 96, that latter resistor being connected between ground and the common terminal between the capacitor 94 and the resistor 95. A further voltage divider including fixed resistors 97 and 98 and a potentiometer 99 is coupled between ground and a source of regulated voltage, $V_{REG}$. The wiper arm of the potentiometer 99 is tied directly to the non-inverting input of the operational amplifier 93. A clamping diode 100, poled as indicated, is connected between the output of the operational amplifier 93 and the junction point between the series connected resistors 95 and 96. The DC restorer circuit 91 causes the voltage signal developed at the output of the low pass filter 18 to be clamped to a voltage established by the setting of the potentiometer 99.

The output from the DC restorer circuit is connected via conductor 101 to the further low pass filter stage 92. This low pass filter is designed to exhibit two poles and includes an operational amplifier 102. The non-inverting input of amplifier 102 receives the output from the DC restorer stage via series connected resistors 103 and 104. A feedback capacitor 106a is connected between the output terminal 105 of the operational amplifier 102 and the common junction between the series connected resistors 103 and 104. A further capacitor 106 is connected directly between the non-inverting input terminal and the reference voltage source $V_R$. A voltage divider including resistors 107 and 108 is connected in series between the source $V_R$ and the output terminal 105 of the low pass filter operational amplifier 102. The inverting input of that amplifier is tied directly to the junction point between the series connected resistors 107 and 108. The signal processing circuitry following the final low pass filter stage 92 may take one of two forms. In the view of FIG. 4, the circuitry is arranged to create a current amplitude which is proportional to an absolute reference stroke volume, the reference being established by the setting of the potentiometer 99. By substituting the circuitry shown in FIG. 5 for that following the junction labeled "X" in FIG. 4, a current signal is produced which is proportional to changes in stroke volume and has no relative reference.

With the foregoing in mind, then, consideration will continue to be given to the embodiment illustrated in FIG. 4, i.e., the arrangement which yields an absolute reference stroke volume current signal. The output from the low pass filter stage 92 is coupled through a resistor 109 to the inverting input of an operational amplifier 110 whose non-inverting input is coupled to a voltage reference source $V_R$ by means of a resistor 111. An integrating capacitor 112 is connected as a feedback element between the output terminal 113 of the operational amplifier 110 and its inverting input terminal. The integrator circuit just described functions to integrate the difference between the actual stroke volume as represented by the envelope of the modulated carrier signal and the reference potential set by the potentiometer 99.

The output from the integrator is applied to a voltage-to-current converter circuit 114. This circuit includes an operational amplifier 115 having its inverting input coupled through a variable resistor 116 to the output from the integrator stage. The non-inverting input of the operational amplifier 115 is coupled through a resistor 117 to the reference voltage source $V_R$. Connected as a feedback element on the voltage-to-current converter 114 is a NPN transistor 118. Specifically, the base electrode of that transistor is coupled to the output of the operational amplifier 115 and its emitter electrode is tied to the inverting input. The resulting current signal $I_{out}$ flowing in the collector circuit of the transistor 118 may be represented mathematically as follows:

$$I_{out} \alpha \int \frac{(V_{sv} + V_{pot.99}) - V_R}{R_{116}}$$

where $V_{sv}$ is the amplitude of the stroke volume at the output of the DC restorer point 101.

This current signal is fed to a so-called current mirror network 119 which functions to generate an output current which is equal to the negative of the input current. The mirror network includes first and second PNP transistors 120 and 121 whose emitters are tied in common to a regulated voltage source $V_{Reg}$ and whose base electrodes are tied in common to the collector electrode of the transistor 118. The collector of the transistor 120 is also tied to the collector electrode of the transistor 118 while the output signal from the current mirror 119 is obtained at the collector electrode of the transistor 121 through coupling resistor 122.

In one application of the invention, the output from the current mirror circuit 119 may be applied to the timing circuit of a cardiac pacer pulse generator in such a way that the normal pacing rate of that pulse generator is made to deviate from a preset rate as a function of the current injected into that timing circuit. A typical, prior art, R-wave inhibited demand pacemaker with which the present invention may be used is fully described in the Anderson et al U.S. Pat. No. 4,041,953. With reference to that patent, the current obtained at the output terminal 123 of the present invention would be connected to the common point between the collector electrode of transistor Q103 and the timing capacitor C101 in the pacer circuit illustrated in FIG. 6a of the Anderson et al Patent 4,041,953. In this way, the current signal contributed by the stroke volume sensing apparatus of the present invention may be injected into the timing capacitor so as to effect a variation in the rate in which pacer pulses are generated in the absence of normal R-wave activity.

OPERATION - FIG. 4

Now that the details of the construction of a first embodiment of the present invention has been set out, consideration will be given to its mode of operation. In this regard, the waveforms set forth in FIGS. 6a through 6i are believed to be helpful to a full and complete understanding of the operation. As has already been indicated, the embodiment of FIG. 4 is designed to provide an absolute reference stroke volume, the reference being set by the potentiometer 99. Furthermore, the control current is assumed to be injected into the timing circuit of a pacer. This current is injected until such time as the integrator capacitor 112 is fully discharged. This does not occur until the stroke volume has returned to or fallen below the preset reference value.

Figure 6:
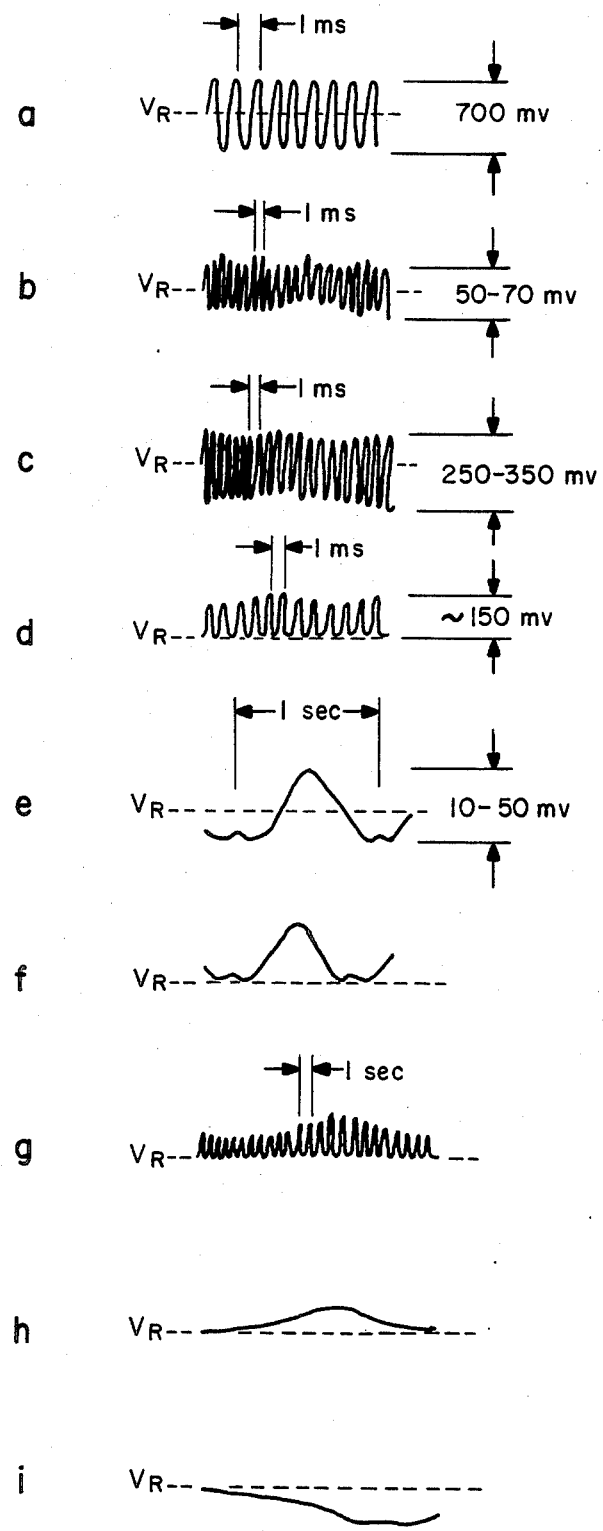
FIGS. 6a through 6i illustrate waveforms at various points in the circuit arrangement of FIG. 4.

FIG. 6a illustrates the signal waveform obtained at the output terminal 32 of the oscillator circuit 10 which signal is applied to the sensing electrodes 12 and 13 disposed on the surface of a lead which is designed to be placed in the right ventricle of the heart. As the heart beats and blood enters and leaves the right ventricle, a change in electrical impedance between the sensing electrodes 12 and 13 takes place. This impedance change results in amplitude modulation of the oscillator output signal and that modulated signal is applied across the inputs of the differential amplifier stage 14. Waveform 6b illustrates the signal appearing at the output of the differential amplifier. Here, the ECG waveform is superimposed on the carrier signal such that the stroke volume modulation is somewhat difficult to observe at this point.

Waveform 6c is illustrative of the waveform observed at the output of the high pass filter network 15, i.e., at the output terminal 65 of the operational amplifier 55. In passing through the high pass filter, the ECG wave is removed such that the stroke volume modulation of the oscillator output (carrier signal) is now quite evident.

Waveform 6d represents the output from the half-wave rectifier 17. As is indicated, the half-wave rectifier serves to remove the negative going peaks from the modulated carrier.

When the half-wave rectified stroke volume modulated carrier signal is next applied to a low pass filter as at 18, the waveform represented by FIG. 6e is representative of what would typically be observed at the output terminal 82. This output constitutes a voltage which is proportional to the instantaneous stroke volume. After passing through the clamping circuit 91, the waveform of FIG. 6f represents the instantaneous stroke volume signal clamped to the voltage $V_R$.

The waveform of FIG. 6g illustrates the clamp output appearing on conductor 101 only with a longer time scale. It shows an increase in stroke volume followed by a decrease. When this signal is applied to the second low pass filter stage 92, the waveform illustrated in FIG. 6h appears at the output terminal 105 of that low pass filter. The clamp for the previous stage is adjusted to give a DC output from the low pass filter of a level $V_R$ when the stroke volume has the desired amplitude.

As is illustrated in FIG. 4, this signal is applied to the integrator circuit 110 and the output of the integrator is represented by the waveform of FIG. 6i. Here, the output is the integrated voltage excursion of the signal from the $V_R$ level and may be represented by the equation set out on page 13, supra. This voltage signal is converted to a current signal by the voltage-to-current converter circuit 114 which produces an output current equal to the input voltage minus the reference voltage divided by the resistance of the variable resistor 116. Accordingly, the output current from the voltage-to-current converter may be represented by the equation set out on page 13 hereof. It is this current that may be coupled through the mirror circuit 119 to the timing circuit of the demand pacer pulse generator or to a control point in other medical electronic apparatus which may broadly be considered as a controlled device.

It will be found that when physiologic demand creates an increase in stroke volume, the current injected into the timing circuit of the cardiac pacer will decrease the timing period of the pulse generator whereby artificial stimulating pulses will be produced at an increased rate. As has already been mentioned, when the heart rate increases, a corresponding decrease in stroke volume results. Thus, the circuit of FIG. 4, when properly connected to a cardiac pacer pulse generator having a current sensitive timing circuit as in the circuit of the aforereferenced Anderson et al patent, will cause that pulse generator to operate at a stimulating frequency which varies in accordance with the deviation of the measured stroke volume from a preset level. When the stroke volume increases, so does the pacing rate. Increases in pacing rate result in a corresponding decrease in stroke volume. Hence, the circuit operates to maintain stroke volume relatively constant at a predetermined threshold level.

The circuit of FIG. 4 may be modified so that instead of continuously operating so as to force the stroke volume signal towards a preset reference, the system will instead be sensitive only to changes in stroke volume without respect to a relative reference. Here, the ventricular pacing rate is made to vary so as to minimize changes in stroke volume. In implementing this alternative arrangement, the portion of the circuitry shown in FIG. 4 to the right of the point labeled "X" is replaced with the circuitry shown in FIG. 5. Specifically, the output from the low pass filter stage 92 is arranged to be coupled through a resistor 124 to the non-inverting input of an operational amplifier 125. A feedback resistor 126 is connected between the operational amplifier's output terminal and its inverting input terminal. A further resistor 127 has one terminal also connected to the inverting input terminal of the amplifier 125 and its remaining terminal connected to the reference voltage source $V_R$. The function of the non-inverting amplifier stage is to introduce a predetermined gain to the voltage output from the low pass filter stage 92. Typically, this gain may be a factor of 10.

The amplified signal appearing at the output of the operational amplifier 125 is next applied as an input to a current controller circuit which is indicated generally by numeral 128. It includes as its active elements a further operational amplifier 129, a first transistor 130 and a second transistor 131. The output from the non-inverting amplifier 125 is coupled through a relatively large capacitor 132 to the non-inverting input of the operational amplifier 129. A further connection is made to this non-inverting input from the center point on a voltage divider network comprised of series connected resistors 133 and 134. This series resistance arrangement is connected between a source of regulated voltage $V_{Reg}$ and ground. The inverting input to the operational amplifier 129 is coupled through a variable resistor 135 to the reference voltage source $V_R$. Resistor 135 is made variable so that the $$\frac{\Delta i \text{ (the change in output current per unit)}}{\Delta V_{sv} \text{ (the change in stroke volume amplitude in volts)}} \cdot$$

can be adjusted. The transistor 130 is connected as a feedback element, having its base electrode coupled to the output of the operational amplifier 129 and its emitter electrode connected to the inverting input of that same amplifier. The collector electrode of the transistor 130 is connected by a conductor 136 to a current mirror circuit 137. The transistor 131 also has its base electrode coupled to the output of the operational amplifier 129 and its collector electrode is connected directly to the non-inverting input of that amplifier. The transistor 131 is biased by means of a potentiometer 138 which is coupled between the voltage source $V_{Reg}$ and $V_R$, the emitter electrode of the transistor 131 being tied to the wiper arm of that potentiometer.

The current mirror circuit is substantially identical in construction to the current mirror circuit 119 of FIG. 4 and includes first and second PNP transistors 139 and 140. The base electrode of these two transistors are tied in common with the collector electrode of the transistor 140 and to the collector electrode of the transistor 130 by way of conductor 136. The emitter electrode of the transistors 139 and 140 are tied together and to the regulated voltage source $V_{Reg}$. The output from the current mirror circuit is fed through a resistor 141 to an output point labeled 142. It is this output point which is arranged to be connected to the timing circuit of the pacer pulse generator as has already been set out in detail when the circuit arrangement of FIG. 4 was under discussion.

It will be recalled that the output signal appearing at point "X" in FIG. 4 is a voltage proportional to stroke volume. This voltage is amplified by the non-inverting amplifier 125 and the resulting output is further processed by the current controller circuit 128 in such a fashion that only changes in the stroke volume are of significance. The changes in stroke volume, of course, are dependent upon the physiologic demand of the body.

The capacitor 132, in combination with the remainder of the circuit, provides a very large time constant, the capacitor acting as a differentiator. Stated otherwise, it comprises a high pass filter with an extremely long time constant. The time constant is determined by the value of the capacitor 132 in microfarads multiplied by the effective resistance of resistors 133 and 134 measured in megohms. This time constant may be set to be approximately in the range from five to thirty-five minutes, 10 minutes being perhaps typical. Under steady-state conditions, the voltage appearing at the non-inverting input of the amplifier 129 will be determined by the magnitude of the DC voltage obtained at the junction point between the resistors 133 and 134. The capacitor 132 will allow only changes in the signal output from the amplifier 125 to pass. The component values are selected such that upon occurrence of changes in the stroke volume voltage signal, approximately thirty minutes, i.e., approximately three time constants, are required for the current signal observed in conductor 136 to return to its quiescent or steady-state level. This thirty minute period corresponds quite closely to that which matches human physiological requirements. That is to say, following significant exercise, approximately twenty to thirty minutes are required for the heart rate to return to the at-rest rate.

The control signal which is developed at the non-inverting input of the operational amplifier 129 is the actual control signal which is, at this point, a function of the changes in stroke volume, not the absolute value of the stroke volume measurement. The amplifier 129 is designed to convert that control signal into a current which may be injected into a conventional cardiac pacer pulse generator in such a fashion that the rate at which ventricular stimulating pulses are generated will be adjusted as a function of that control signal or which may be applied to other apparatus where stroke volume monitoring and/or response to changes in stroke volume is desired.

Referring momentarily to FIG. 6a of the Anderson et al U.S. Pat. No. 4,041,953, the transistors Q101 and Q102, along with the resistors R103 and R104, comprise a constant current generator. That current source sets up a voltage, then, that allows a current through transistor Q103 for charging up the pulse generator's timing capacitor C101. That last-mentioned capacitor forms a portion of the RC time constant of the oscillator portion of the pacer pulse generator. By injecting current at the point indicated, the charging time of the capacitor C101 is decreased and the ventricular stimulating pulses appearing across the Heart+ and Heart− terminals of the pulse generator circuit will increase, assuming that naturally occuring R-waves do not inhibit the operation of that demand pacer.

Figure 5:
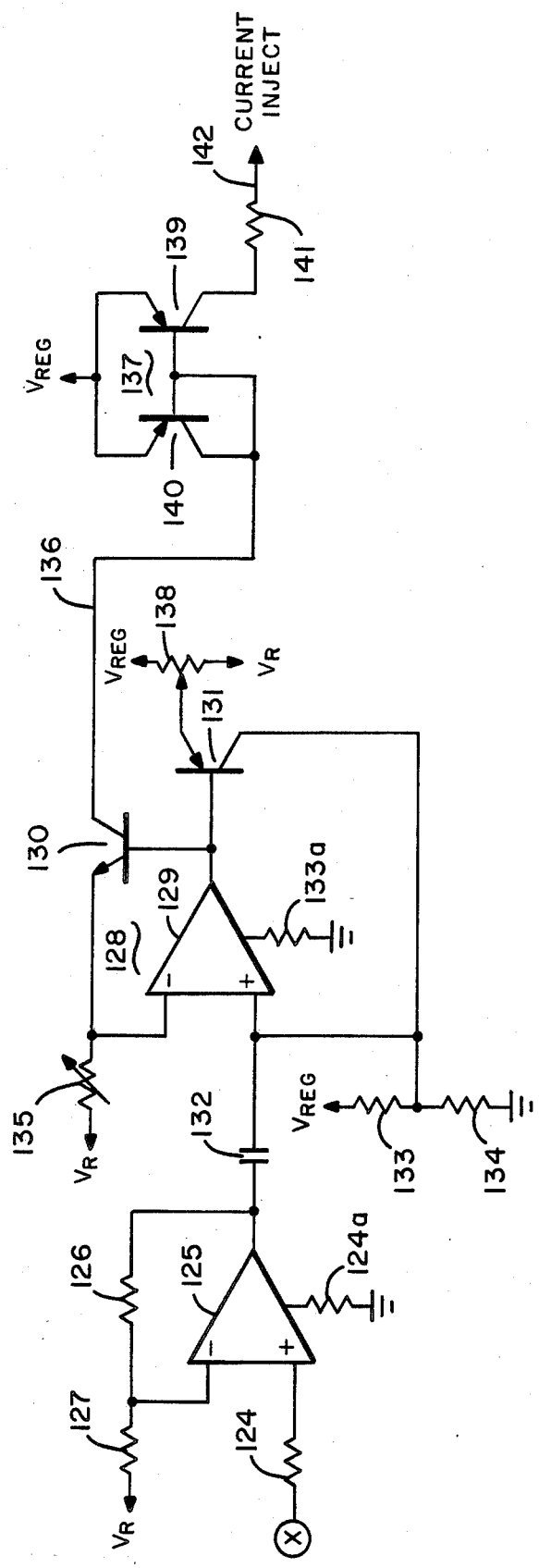
FIG. 5 is a modification of the embodiment in FIG. 4 whereby the control signal is determined by changes in stroke volume without reference to a pre-established threshold.

Summarizing, momentarily, the circit of FIG. 5, when coupled to the tie point "X" in FIG. 4 and used as a replacement for the circuitry in FIG. 4 located downstream from that tie point, provides an injected current which is proportional to changes in stroke volume. Only increases in stroke volume are sensed. Decreases in stroke volume result in the discharge of the capacitor 132 which, as it discharges, decreases the injected current level.

With no limitation intended and for illustrative purposes only, the following table sets forth typical component values which may be used in implementing the stroke volume sensing and pacer control apparatus of the present invention.

TABLE ONE

| COMPONENT VALUES | | | |
|---|---|---|---|
| RESISTORS | VALUE | | |
| 33,45,48,60,62, 67,71,76,88,89, 107,108,122, 124,127,141 | 1 M | CAPACITORS | VALUE |
| | | 31 | 200 pf |
| | | 37 | 0.56 uf |
| | | 44,47 | 0.1 uf |
| 35 | 3.3 M | 52,56,63,64 | 0.001 uf |
| 36 | 1.4 M | 77 | 5 pf |
| 40 | 2 K | 86,87 | 0.033 uf |
| 41 | 100 K | 94 | 10 uf |
| 43,49,50,59a, 72a,109,111,126 | 10 M | 106,106a,112 | 4.7 uf |
| | | 132 | 25 uf |
| 50a | 5 M | OP AMPS | TYPE |
| 58,59 | 78 K | 29,39,46,54,55, 70,79,93,102, 110,115,125,129 | NATIONAL LM 4250 or INTERSIL ICL 8023 |
| 66 | 1.8 M | | |
| 66a,68 | 150 K | | |
| 68a,103,104 | 3 M | | |
| 72,117 | 500 K | | |
| 83 | 50 K | TRANSISTORS | TYPE |
| 84,85 | 910 K | 118,130 | 2 N 2484 |
| 85a,96,108a, 111a,117a,124a, 133,133a | 22 M | 120,121,131, 139,140 | 2 N 3799 |
| | | VOLTAGES | TYPE |
| 95 | 2 M | $V_R$ | 0.875 V |
| 97,98 | 4.7 M | $V_{Reg}$ | 1.75 V |
| 99,135 | 1 M Var. | | |
| 116 | 2 M Var. | | |
| 134 | 12 M | | |
| 138 | 5 M Var. | | |

The invention has been described herein in considerable detail, in order to comply with the Patent Statutes and to provide those skilled in the art with information needed to apply the novel principles and to construct and use such specialized components as are required. However, it is to be understood that the invention can be carried out by specifically different equipment and devices. For example, the control current proportional to stroke volume change may be used in conjunction with an implantable infusion pump for administering such drugs as dobutamine isoprotorenol or nitroprusside whereby stroke volume may be maintained at a desired value. Alternatively, the demodulated waveform or control signal may be used directly by other diagnostic equipment. By appropriately utilizing the information derived from the ventricular impedance, it would be possible to measure stroke volume without having to resort to thermal dilution or other techniques. Hence, various modifications, both as to equipment details and operating procedures can be effected without departing from the scope of the invention itself.

What is claimed is:

1. Apparatus for applying therapy to a patient based upon the hemodynamic state of said patient's body, comprising in combination:
    (a) intracardiac ventricular impedance sensing means for sensing the stroke volume in only one ventricular chamber of the heart;
    (b) means coupled to said sensing means for developing a control signal varying as a function of changes in said stroke volume;
    (c) patient therapy means having controllable rate means for establishing the rate at which prescribed therapy is administered to the patient; and
    (d) means for applying said control signals to said controllable rate means to change said rate in relation to said changes in stroke volume.

2. Apparatus as in claim 1 wherein said intracardiac impedance sensing means comprises:
    (a) an elongated electrical lead having a plurality of conductors extending the length thereof within an insulating sheath, said conductors individually terminating distally at plural spaced apart electrode means exposed on the exterior of said sheath with said electrode means located in one of the ventricular chambers of the heart;
    (b) a source of an alternating current carrier signal whose frequency is in the range of from 500 to 5,000 Hertz electrically coupled to the proximal ends of said plurality of conductors for creating an alternating current voltage between said spaced electrodes; and
    (c) further means coupled to said conductor means for detecting modulation of said alternating current carrier signal occasioned by the beating action of said patient's heart, said modulation being a function of electrical impedance changes between ones of said electrode means in said one of said ventricular chambers.

3. Apparatus as in claim 2 wherein said means for developing an electrical control signal proportional to changes in stroke volume comprises:
    (a) signal processing means coupled to said further means for converting the modulation envelope waveform of said carrier signal into an output proportional to changes in stroke volume.

4. Apparatus as in claim 3 and further including means in said signal processing means for establishing a fixed reference value such that said output is proportional to changes in stroke volume from said fixed reference value.

5. A variable rate cardiac pacer apparatus responsive to metabolic needs of the patient comprising in combination:
    (a) a source of alternating current carrier signals of a predetermined frequency in the range of from 500 to 5,000 Hertz
    (b) an endocardial electrical lead having at least two spaced apart sensing electrodes and a stimulating electrode, said sensing electrodes being located proximally of said stimulating electrode such that when said stimulating electrode is proximate the apex of one ventricular chamber, said sensing electrodes are also within said one chamber said lead having conductors coupling said source of carrier signals to said pair of sensing electrodes;
    (c) sense amplifier means coupling through said lead to said pair of sensing electrodes for receiving and amplifying modulated electrical signals developed across said sensing electrodes;
    (d) high pass filter means connected to receive the output from said sense amplifier means for passing said carrier signals while attenuating any electrical artifacts picked up at said sensing electrodes of a frequency which is less than said predetermined frequency of said carrier signals;
    (e) demodulator circuit means including low pass filter means coupled to the output of said high pass filter means for demodulating said modulated carrier signal and recovering the modulating signal therefrom, said modulating signal being proportional to instantaneous stroke volume of the patient's heart;
    (f) means coupled to said low pass filter for developing a control current proportional to changes in said modulating signal;
    (g) a cardiac pacer pulse generator having a timing means for determining the rate at which heart stimulating pulses will be generated;
    (h) means applying said control current to said timing means; and
    (i) means coupling said generated stimulating pulses to said stimulating electrode on said lead.

6. Apparatus as in claim 5 wherein said means for developing a control current proportional to changes in said modulating signal comprises:
    (a) means for establishing a fixed reference potential; and
    (b) integrator circuit means coupled to receive said modulating signal and said fixed reference potential for integrating the difference between said modulating signal and said fixed reference potential.

7. A method of controlling the rate at which cardiac stimulating impulses are generated by a cardiac pacer pulse generator of the type having a variable timing means defining the period of said stimulating impulses, comprising:
    (a) positioning an endocardial lead having spaced apart electrodes proximate its distal end in the vascular system such that said electrodes are in only one ventricular chamber of the heart;
    (b) applying a high frequency carrier signal to said lead and across said spaced electrodes;
    (c) detecting the modulation of said carrier signal occasioned by the inflow and outflow of blood in said one chamber during diastole and systole;

(d) developing a control signal proportional to changes in the detected modulation; and (e) applying said control signal to said variable timing means of said cardiac pacer pulse generator to alter the rate at which stimulating pulses are generated.

8. A method of controlling the rate at which therapy is administered to a patient as a function of the hemodynamic state of said patient's body, comprising:

(a) positioning an endocardial lead having spaced apart electrodes proximate its distal end in the vascular system such that said electrodes are in only one ventricular chamber of the heart;

(b) applying a high frequency carrier signal to said lead and across said spaced electrodes;

(c) detecting the modulation of said carrier signal occasioned by the inflow and outflow of blood from said one chamber during diastole and systole;

(d) developing a control signal indicative of the changes in the detected modulation; and (e) utilizing said control signal to vary the rate at which said therapy is administered.

9. Cardiac stimulating apparatus having means for adjusting the frequency of stimulation as a function of physiologic demand, comprising in combination:

(a) a pulse generator having timing means therein for determining the frequency at which cardiac stimulating pulses are produced;

(b) means for conveying said cardiac stimulating pulses to a patient's heart;

(c) impedance plethysmographic means including sensing means for measuring the stroke volume solely within one ventricular chamber of said heart; and (d) means coupled to said impedance plethysmographic means for producing a control signal proportional to changes in stroke volume of the patient's heart; and (e) means coupling said control signal to said pulse generator for altering the operation of said timing means whereby the frequency at which stimulating pulses are produced varies with changes in stroke volume.

10. Apparatus as in claim 9 wherein said means for producing a control signal comprises:

(a) endocardial lead means having a pair of spaced-apart electrodes proximate the distal end of said lead means such that when said lead means is inserted in the vascular system, said electrodes are in only one ventricular chamber of the heart;

(b) means for applying a carrier signal via said lead means to said electrodes, said carrier signal having a frequency which is in the range of from 500 to 5,000 Hertz;

(c) demodulation means coupled to said lead means for detecting changes in amplitude of said carrier signal picked up by said electrodes which are occasioned by instantaneous changes in the volume of the heart;

(d) integrating means coupled to said demodulation means for producing a direct current signal proportional to said changes in said carrier signal over a predetermined time interval; and (e) means for applying said control signal to said timing means in said pulse generator for changing the frequency at which cardiac stimulating pulses are produced in accordance with changes in the stroke volume of the heart.

11. Apparatus as in claim 10 wherein said carrier signal applied to said electrodes is of an amplitude and frequency insufficient to evoke electrically stimulated systoles.

12. A cardiac pacer system comprising:

(a) pulse generator means having a variable timing means for producing a cardiac stimulating impulses at a rate determined by said variable timing means;

(b) an endocardial lead coupled to the output of said pulse generator means and having a stimulating tip electrode and at least two additional electrodes proximally spaced a predetermined distance from said tip electrode so as to be located solely within one ventricular chamber of the heart when said stimulating tip electrode is disposed at the apex of the heart;

(c) means for applying an alternating current carrier signal of a predetermined amplitude and frequency between said two additional electrodes, said amplitude and frequency of said carrier signal being such that electrically stimulating systoles are not evoked by said carrier signal and said predetermined frequency being in the range of from 500 to 5,000 Hertz;

(d) high-pass filter means coupled to said pair of additional electrodes for attenuating signals picked up by said pair of electrodes which are of a lesser frequency than said predetermined frequency;

(e) demodulator means coupled to the output of said high-pass filter means for developing a control signal proportional to changes in amplitude of said alternating current carrier signal; and (f) means for applying said control signal to said timing means in said pulse generator means whereby the rate of the stimulating pulses produced at said tip electrode is determined in part by said control signal.

13. Apparatus as in claim 12 wherein said demodulator means comprises:

(a) a half-wave rectifier circuit having an input and an output, said input being coupled to receive modulated carrier signals from said high-pass filter means;

(b) first low-pass filter means having an input for receiving the output from said half-wave rectifier and a cut-off frequency characteristic which is less than the frequency of said carrier signal, but greater than the expected frequency of a heartbeat; and (c) second low-pass filter means coupled to receive the output from said first low-pass filter means, said second low-pass filter means having a cut-off frequency which is lower than the expected frequency of a heartbeat for producing a direct current voltage proportional in amplitude to changes in amplitude of said modulated carrier signals.

14. A variable rate cardiac pacer apparatus responsive to metabolic needs of the body, comprising in combination:

(a) intracardiac impedance plethysmography means for sensing changes in stroke volume in only one ventricular chamber of a mammalian heart;

(b) means coupled to said intracardiac impedance plethysmography means for developing a control signal proportional to said changes;

(c) cardiac pacer pulse generating means having timing means for determining the rate at which said pulse generator means produces output cardiac stimulating signals; and (d) means for applying said control signals to said timing means to change said rate in relation to said changes in stroke volume.

* * * * *